(12) United States Patent
Commandeur

(10) Patent No.: US 6,888,036 B2
(45) Date of Patent: May 3, 2005

(54) MONO-AND POLYBENZYL-1,2,3,4-TETRAHYDRONAPHTHALENE COMPOSITIONS, USE OF SAID COMPOSITIONS OR MIXTURE OF MONOBENZYL-,1,2,3,4-TETRAHYDRONAPHTHALENE AS HEAT TRANSFER FLUID

(75) Inventor: Raymond Commandeur, Vizille (FR)

(73) Assignee: Arkema, Puteaux (FR)

( * ) Notice: Subject to any disclaimer, the term of this patent is extended or adjusted under 35 U.S.C. 154(b) by 0 days.

(21) Appl. No.: 10/240,094

(22) PCT Filed: Mar. 27, 2001

(86) PCT No.: PCT/FR01/00932

§ 371 (c)(1),
(2), (4) Date: Mar. 10, 2003

(87) PCT Pub. No.: WO01/72672

PCT Pub. Date: Oct. 4, 2001

(65) Prior Publication Data

US 2004/0077907 A1 Apr. 22, 2004

(30) Foreign Application Priority Data

Mar. 29, 2000 (FR) ............................................. 00 03946
Feb. 1, 2001 (FR) ............................................. 01 01355

(51) Int. Cl.⁷ .......................... C07C 13/48; C07C 2/86; C09K 5/10
(52) U.S. Cl. ................................ 585/26; 585/1; 252/73
(58) Field of Search ........................................ 585/1, 26

(56) References Cited

U.S. PATENT DOCUMENTS

| | | | | |
|---|---|---|---|---|
| 3,909,432 A | * | 9/1975 | McGuire et al. ............ 585/456 |
| 4,225,747 A | * | 9/1980 | Vecellio ..................... 174/25 C |
| 4,604,491 A | * | 8/1986 | Dressler et al. ................ 585/26 |
| 4,665,275 A | * | 5/1987 | Yoshida et al. ................ 585/27 |
| 4,737,297 A | * | 4/1988 | Yoshida et al. .............. 508/110 |
| 4,755,317 A | * | 7/1988 | Minokami et al. ............. 252/73 |
| 4,800,032 A | * | 1/1989 | Murphy ...................... 508/232 |
| 5,001,276 A | * | 3/1991 | Klaus et al. ................. 568/609 |
| 5,055,622 A | * | 10/1991 | Klaus et al. ................. 568/609 |
| 5,466,861 A | | 11/1995 | Dawson et al. |
| 6,239,320 B1 | * | 5/2001 | Mendoza et al. ............ 585/6.3 |
| 6,350,927 B2 | * | 2/2002 | Mendoza ..................... 585/6.3 |

FOREIGN PATENT DOCUMENTS

JP 49 105781 A * 10/1974

OTHER PUBLICATIONS

PCT Search Report– PCT/FR01/00932.*

PCT Preliminary Examination Report– PCT/FR01/00932.*

Database WPI, Section Ch, Week 197521, AN 1975–34982W, XP002152852, Derwent Publications Ltd., London, GB.

* cited by examiner

*Primary Examiner*—Ellen M. McAvoy
(74) *Attorney, Agent, or Firm*—Millen, White, Zelano & Branigan, P.C.

(57) ABSTRACT

The invention concerns compositions comprising a mixture of mono- and polybenzyl-1,2,3,4-tetrahydronaphthalenes. The invention also concerns said compositions or a mixture of monobenzyl-1,2,3,4-tetrahydronaphthalene isomers as heat transfer fluid. Said compositions or the mixture of monobenzyl-1,2,3,4-tetrahydronaphthalene isomers are obtained by the action of benzyl chloride on 1,2,3,4-tetrahydronaphthalene in the presence of $FeCl_3$.

11 Claims, No Drawings

MONO-AND POLYBENZYL-1,2,3,4-TETRAHYDRONAPHTHALENE COMPOSITIONS, USE OF SAID COMPOSITIONS OR MIXTURE OF MONOBENZYL-,1,2,3,4-TETRAHYDRONAPHTHALENE AS HEAT TRANSFER FLUID

The present invention relates to mono- and polybenzyl-1,2,3,4-tetrahydronaphthalene compositions.

These compositions comprise a mixture of the following compounds (Y), (Y1), and (Y2):

(Y) is a mixture of monobenzyl-1,2,3,4-tetrahydronaphthalene isomers of formula:

(Y)

(Y1) is a mixture of monobenzylation compounds of (Y), of formulae:

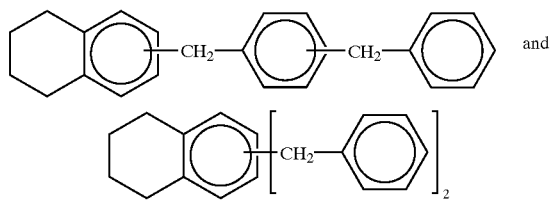

and (Y1)

(Y2) is a mixture of mono- or polybenzylation compounds of (Y1), of formulae:

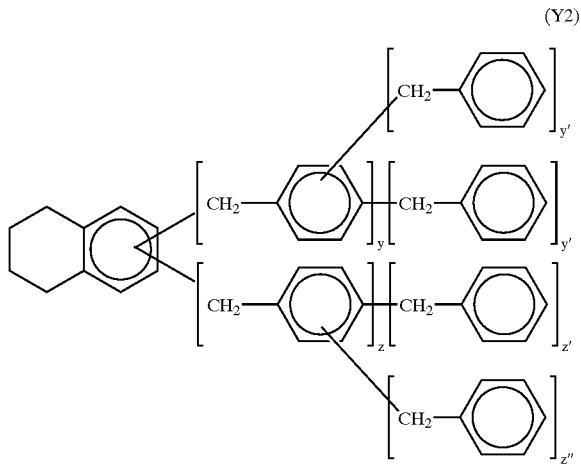

(Y2)

where y and z=0, 1 or 2; y', y'', z', z''=0 or 1, with the provisos that y+z is never 0, that y'+y''+z'+z''≧1, and that y+z+y'+y''+z'+z''≧3.

The invention likewise relates to the use of said compositions or else of a mixture of monobenzyl-1,2,3,4-tetrahydronaphthalene isomers of formula:

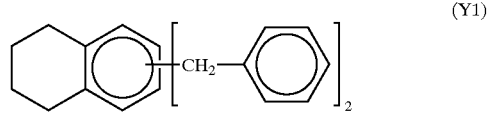

(Y1)

as heat transfer fluid.

Heat transfer fluids are widely used in order to ensure rigorous control of temperatures in chemical industry operations and are required to possess a certain number of physicochemical characteristics Accordingly, heat transfer fluids which must be used within a very wide temperature range, i.e., ranging from −30° C. to +400° C., are required to have not only good heat transfer but also a high boiling temperature at atmospheric pressure, good thermal stability, low viscosity over a wide range of temperatures, even at low temperature during, in particular, their employment, low tendency to corrode the materials of the apparatus, and low sensitivity to oxidation. They must also carry little risk to the environment in case of leakage, and also little risk of fire.

Among all of these criteria, the thermal stability is a determinant criterion and is the concern of manufacturers and producers of heat transfer fluids.

The degradation of a heat transfer fluid is typically accompanied by the formation both of volatile products, which lower the flash point of the heat transfer fluid, and of heavy products, which raise the viscosity and also lower the heat transfer coefficient Numerous publications propose products intended to meet all of the aforementioned criteria, but the range of products which can be used in particular at atmospheric pressure within a temperature range from ambient to approximately 350° C. is limited.

In the article by Commandeur et al titled: "Une nouvelle famille de fluides thermiques hautes performances [A new family of high performance thermal fluids]" (Inf. Chimie No. 376, 1996, pages 93–96) and in Kirk-Othmer Encyclopaedia of Chemical technology—4th edition, Vol. 12, pages 993 to 1006, a list can be found of the principal commercially available heat transfer fluids.

By way of illustration of such products, mention is made in particular of the mixtures of isomers of dibenzyltoluene, partially hydrogenated terphenyls, benzenealkylates, and mixtures of biphenyl and diphenyl ether.

Furukawa Y. et al. describe, in patent application JP 74 105 781 published Oct. 7, 1974, heat transfer fluids consisting essentially of compounds of formula:

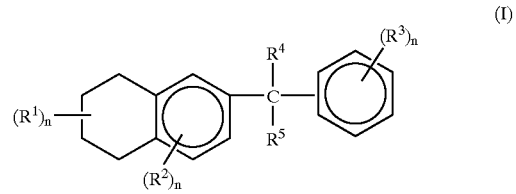

(I)

in which $R^1$, $R^2$, $R^3$, $R^4$, and $R^5$ is selected from the hydrogen atom and a lower alkyl radical such as $CH_3$—, and n is 1 or 2.

The thermal stability of these products has been evaluated under nitrogen pressure at temperatures of at most 340° C.

For instance, 1-phenyl-1-(5,6,7,8-tetrahydro-2-naphthyl) ethane (formula (I) in which $R^1=R^2=R^3=R^4=H$, $R^5=CH_3$—, n=1) was tested at 340° C. under a nitrogen pressure of 15 kg/cm² for 14 days and did not show any significant change in flash point, in its viscosity, and its color.

The mono- and polybenzyl-1,2,3,4-tetrahydronaphthalene compositions and the mixture of monobenzyl-1,2,3,4-tetrahydronaphthalene isomers of the present invention meets all of the aforementioned criteria. In particular, they exhibit a thermal stability which allows them to be used at temperatures as high as 370° C. under pressures greater than or equal to atmospheric pressure while retaining their excellent heat transfer properties.

In accordance with the present invention, the compounds (Y), (Y1), and (Y2) are present in compositions in accordance with the following proportions by weight:

compounds of formula (Y): between 60% and 90%,
compounds of formula (Y1): between 9% and 35%,
compounds of formula (Y2): between 0.1% and 10%.

In accordance with the present invention, the mixture of monobenzyl-1,2,3,4-tetrahydronaphthalene isomers comprises a mixture of from 30% to 40% by weight of 5-benzyl-1,2,3,4-tetrahydronaphthalene and from 70% to 60% by weight of 6-benzyl-1,2,3,4-tetrahydronaphthalene.

The mono- and polybenzyl-1,2,3,4-tetrahydronaphthalene compositions and the mixture of monobenzyl-1,2,3,4-tetrahydronaphthalene isomers may be obtained by reacting benzyl chloride with a large molar excess of 1,2,3,4-tetrahydronaphthalene in the presence of an inorganic halide or else of a protic acid.

Use will be made of a molar 1,2,3,4-tetrahydronaphthalene/benzyl chloride ratio which is preferably equal to approximately 4 when it is desired to obtain compositions comprising a mixture of compounds (Y), (Y1), and (Y2), and at least equal to 4 and, preferably, between 8 and 12 when it is desired to obtain the monobenzyl-1,2,3,4-tetrahydronaphthalene isomer mixture.

This reaction takes place in practice at a temperature of between 30° C. and 150° C. and, preferably, between 50° C. and 100° C.

Among inorganic halides, use may be made of ferric chloride, antimony trichloride, titanium tetrachloride or else aluminum chloride in amounts by weight relative to the reactants employed of customarily between 50 ppm and 1% and preferably between 100 ppm and 0.5%. Preference will be given to using ferric chloride. The protic acids may likewise be used: sulfuric acid, for example, at a concentration by weight of between 70 and 95%. It is also possible to employ zeolites or else certain inorganic oxides.

Following distillation of the excess 1,2,3,4-tetrahydronaphthalene, the inorganic halide or the protic acid is removed by any known technique such as: washing with water followed by drying when using a protic acid or treatment with sodium methoxide as described in Patent EP 306 398 B1 when using an inorganic halide.

The product thus treated is subjected either to flash evaporation in order to remove the traces of impurities originating either from the raw materials or from the process, or having an accidental origin, and any catalyst residues, or to fractional distillation so as to obtain fractions comprising compounds (Y), (Y1) and/or (Y2). From these fractions it is possible to, prepare compositions containing well-defined amounts of compounds (Y), (Y1), and (Y2).

The characterization of the compounds (Y), (Y1), and (Y2) and their amounts in the various distillation fractions, and the characterization of the mixture of monobenzyl-1,2,3,4-tetrahydronaphthalene isomers, may be carried out by carbon-13 proton NMR analysis and by gas chromatography/mass spectrometry coupling.

It would not be depart from the scope of the invention to use, for the preparation of the compositions comprising compounds (Y), (Y1), and (Y2), instead of 1,2,3,4-tetrahydronaphthalene, a mixture of naphthalene compounds with greater or lesser degrees of hydrogenation. These mixtures generally comprise from 80% 90% by weight of 1,2,3,4-tetrahydronaphthalene, the remainder to 100% consisting of variable amounts of decahydronaphthalene and naphthalene.

The examples which follow illustrate the invention.

EXAMPLE 1

Preparation of a Composition Comprising Compounds (Y), (Y1), and (Y2)

A 10 l reactor equipped with a rotary stirrer, an ascending condenser, a nitrogen injector, a thermometer sheath, a dropping funnel, and heating means is charged with 5404 g of 1,2,3,4-tetrahydronaphthalene with a purity of 98.5%, corresponding to 40.94 moles. The product is heated to 120° C. with nitrogen blanketing and stirring.

The outlet of the condenser is then connected to a water bubbler.

6.7 g of anhydrous $FeCl_3$ are added to the reactor, followed, still with nitrogen blanketing, by 1295.4 g of benzyl chloride with a purity of 99%, corresponding to 10.24 moles, over 3 hours 30 minutes. The molar 1,2,3,4-tetrahydronaphthalene/benzyl chloride ratio is 4.

At the end of introducing the benzyl chloride, it is found that the amount of HCl given off and trapped in the bubbler is 9.14 moles.

The amount by weight of benzyl chloride present in the reaction mixture is 0.74%.

The reaction is continued with stirring and nitrogen blanketing at 120° C. for 1 hour and then at 130° C. for 1 hours.

The total amount of HCl given off and trapped in the bubbler is 10.2 moles.

The final amount of benzyl chloride in the reaction mixture is approximately 0.02% by weight. After cooling to ambient temperature and with nitrogen blanketing, the contents of the reactor (6325 g) are then placed in a 10 l round-bottomed distillation flask atop which there is an adiabatic column 50 cm high which is packed with glass spirals (column efficiency equal to approximately 3 theoretical plates) surmounted by a single distillation head and a condenser.

Unconverted 1,2,3,4-tetrahydronaphthalene is recovered by distillation under a pressure of 40 mm of mercury.

Distillation is performed over 4 hours at a still temperature ranging from 130° C. to 239° C. and an overhead temperature ranging from 115° C. to 118° C. for the majority of the distillation, with an increase to 142° C. at the end of distillation.

4200 g of a colorless liquid are recovered which has a 1,2,3,4-tetrahydronaphthalene content of more than 98.5% and can be recycled to a subsequent operation.

The distillation bottoms (2105 g), containing less than 0.14% by weight of 1,2,3,4-tetrahydronaphthalene, are subsequently subjected to an operation to remove the small quantities of residual organic chlorine, an operation which consists in treating said distillation bottoms with approximately 21 g of $CH_3ONa$ in powder form (1% by weight relative to the weight of the product to be treated) in a reactor with stirring and with nitrogen blanketing at 300° C. for 3 hours.

The product thus treated, containing 77.3% by weight of compounds of formula (Y), 18.6% by weight of compounds of formula (Y1), and 2.8% by weight of compounds of formula (Y2), is subjected to fractional distillation in the distillation apparatus used above.

The distillation is conducted in a first stage under a pressure of 18 mm of Hg at still temperatures ranging from 220° C. to 294° C. and then in a second stage, following removal of the packing from the column, under a pressure of 12 mm of Hg at still temperatures ranging from 294° C. to 344° C.

Various fractions are recovered which have the weight contents (%) of mono- and polybenzyl-1,2,3,4-tetrahydronaphthalenes as reported in Table 1 below:

TABLE 1

| Fraction | Weight (g) | Boiling temperature (° C.) | Pressure (mmHg) | BTHN (%) | DBTHN (%) | TBTHN (%) |
|---|---|---|---|---|---|---|
| 1 | 124.5 | 200–218 | 18 | 95.5 | — | — |
| 2 | 1400 | 218–220 | 18 | >98.8 | 0.2 | — |
| 3 | 13.5 | 220–290 | 12 | 20.37 | 66.3 | 1.3 |
| 4 | 440 | 290–305 | 12 | 0.44 | 92.2 | 5.2 |
| 5 | 69 | 305–330 | 12 | 0.35 | 45.7 | 53.5 |
| 6 | 14 | 330–334 | 12 | 0.7 | 4 | 93.3 |

In this Table 1:

BTHN denotes monobenzyl-1,2,3,4-tetrahydronaphthalene (formula (Y)) which is a mixture of 6-benzyl-1,2,3,4-tetrahydronaphthalene (65% by weight) and 5-benzyl-1,2,3,4-tetrahydronaphthalene (35% by weight).

DBTHN denotes the compounds of formula (Y1).

TBTHN denotes a mixture of compounds of formula (Y2) in which $y+z+y'+y''+z'+z''=3$.

The residue of approximately 40 g contains approximately 20% by weight of TBTHN and also unidentified heavy products and the inorganic part.

The initial fractions are colorless liquids. The hind fractions are yellow.

The compositions of the invention may easily be prepared (obtained), mixing the fractions obtained above, by distillation so as to give a composition containing by weight:
a % of BTHN (Y),
b % of DBTHN (Y1),
c % of TBTHN (Y2).

Accordingly, a composition has been obtained which is denoted PBTHN hereinafter and contains approximately:
 80% by weight (79.96%) of a mixture of monobenzyl-1,2,3,4-tetrahydronaphthalene isomers (compounds of formula (Y));
 19% by weight (18.98%) of compounds of formula (Y1);
 1% by weight (1.06%) of formula Y(2) in which $y+z+y'+y''+z'+z''=3$)
by mixing, for example, 83 parts by weight of fraction 2 with 21 parts by weight of fraction 4.

EXAMPLE 2

Preparation of a Mixture of Monobenzyl-1,2,3,4-tetrahydronaphthalene Isomers (Y)

A 6 liter reactor equipped with a rotary stirrer, an ascending condenser, a nitrogen injector, a thermometer sheath, a dropping funnel, and heating means is charged with 3890 g of 1,2,3,4-tetrahydronaphthalene with a purity of 98.5%, corresponding to 22.97 moles. The product is heated to 120° C. with nitrogen blanketing and stirring.

The outlet of the condenser is subsequently connected to a water bubbler.

4.3 g of anhydrous $FeCl_3$ are added to the reactor, followed, still with nitrogen blanketing, by 375 g of benzyl chloride with a purity of 99%, corresponding to 2.95 moles, over 3 hours 30 minutes. The molar 1,2,3,4-tetrahydronaphthalene/benzyl chloride ratio is 10.

At the end of introduction of the benzyl chloride, it is found that the amount of HCl given off and trapped in the bubbler is 2.21 moles.

The reaction is continued with stirring and nitrogen blanketing at 120° C. for 1 hour.

The total amount of HCl given off and trapped in the bubbler is 2.4 moles, one portion remaining solubilized in the reaction mixture.

The final amount of benzyl chloride in the reaction mixture is approximately 0.02% by weight. After cooling to ambient temperature and with nitrogen blanketing, the contents of the reactor (4144 g) are subsequently placed in a 6 l round-bottomed distillation flask atop which there is an adiabatic column 50 cm high which is packed with glass spirals (column efficiency equal to approximately 3 theoretical plates) and surmounted by a single distillation head and a condenser.

Unconverted 1,2,3,4-tetrahydronaphthalene is recovered by distillation under a pressure of 20 mm of mercury.

Distillation is carried out over 4 hours at a still temperature ranging from 105° C. to 213° C. and an overhead temperature ranging from 92° C. to 94° C. for the majority of the distillation, with a rise to 159° C. at the end of distillation.

3483 g of a colorless liquid are recovered which has a 1,2,3,4-tetrahydronaphthalene content of more than 98.5% and can be recycled to a subsequent operation.

The distillation bottoms (647 g), containing less than 0.02% by weight of 1,2,3,4-tetrahydronaphthalene, are subsequently subjected to an operation to remove small quantities of residual organic chlorine, an operation which consists in treating said distillation bottoms with approximately 6.5 g of $CH_3ONa$ in powder form (1% by weight relative to the weight of the product to be treated) in a reactor with stirring and nitrogen blanketing at 300° C. for 3 hours.

The product thus treated is subjected to fractional distillation in the distillation apparatus used above.

The distillation is conducted under a pressure of 18 mm of Hg at still temperatures ranging from 220° C. to 303° C.

569 g are recovered of a mixture of monobenzyl-1,2,3,4-tetrahydronaphthalene isomers which is in a mixture of 6-benzyl-1,2,3,4-tetrahydronaphthalene and 5-benzyl-1,2,3,4-tetrahydronaphthalene and has a boiling point at atmospheric pressure of 350° C., a viscosity at 20° C. of 21 $mm^2/s$, and a chlorine content of 1 ppm. The yield relative to the benzyl chloride employed is 86.87%.

The mixture of 6-benzyl-1,2,3,4-tetrahydronaphthalene and 5-benzyl-1,2,3,4-tetrahydronaphthalene was characterized firstly by $^{13}C$ NMR in $CDCl_3$ as solvent (coupled and decoupled $^1H$), which allows the structures of the 2 isomers to be identified, and $^1H$ NMR in $CDCl_3$ and $C_6D_6$, which makes it possible to give the proportions of the two isomers, and secondly by gas chromatography-mass spectrometry coupling, which makes it possible to confirm the structure and also the proportions of the two isomers. In particular, 5-benzyl-1,2,3,4-tetrahydronaphthalene is characterized by an intense m/z fragmentation peak at 144 which is attributed to the radical cation obtained following the elimination of benzene from the 5-benzyl-1,2,3,4-tetrahydronaphthalene radical cation.

The techniques used indicate that the mixture of monobenzyl-1,2,3,4-tetrahydronaphthalene isomers contains 35% by weight of 5-benzyl-1,2,3,4-tetrahydronaphthalene and 65% by weight of 6-benzyl-1,2,3,4-tetrahydronaphthalene.

The thermal stability of the composition prepared in Example 1, denoted PBTHN, and of the mixture of monobenzyl-1,2,3,4-tetrahydronaphthalene isomers prepared in Example 2, and denoted BTHN, was evaluated in comparison to a heat transfer fluid commercialized by DOW CHEMICAL COMPANY under the name DOWTHERM RP which is a mixture of 1,2,3,4-tetrahydro-5-(1phenylethyl)naphthalene and 1,2,3,4-tetrahydro-6-(1-phenylethyl)naphthalene.

The tests were carried out at 370° C. for 160 hours for PBTHN and at 370° C. for 160 hours and 340 hours for BTHN in a 200 ml stainless-steel autoclave equipped with a thermometer sheath and a manometer. 50 g of the heat transfer fluid to be tested are introduced, and the autoclave is blanketed with nitrogen, closed and then placed in an electrically heated sand bath. Regulation makes it possible to hold the temperature of the heat transfer fluids constant at 370° C.

The results are reported in Tables 2 and 3, and demonstrate the better thermal characteristics of the PBTHN composition and of the BTHN in accordance with the invention.

TABLE 2

|  | PBTHN | DOWTHERM RP |
|---|---|---|
| Pressure at end of test (in bars): |  |  |
| at 370° C. | 10.2 | 10 |
| at 20° C. | 4.5 | 4 |
| Appearance of the product at end of test: | yellow | orange |
| Viscosity (in mm²/s) at 20° C.: |  |  |
| initial | 38 | 45 |
| at end of test | 29 | 22 |
| GC analysis (% by weight): |  |  |
| 1-ring compounds | 2.15 | 3.8 |
| 2-ring compounds | 2.19 | 5.2 |

TABLE 3

|  | BTHN | | DOWTHERM RP | |
|---|---|---|---|---|
|  | 160 hours | 340 hours | 160 hours | 340 hours |
| Pressure at end of test (in bars): |  |  |  |  |
| at 370° C. | 7.5 | 13.5 | 10 | 18.5 |
| at 20° C. | 3.5 | 6.3 | 4 | 6.8 |
| Viscosity (in mm²/s) at 20° C.: |  |  |  |  |
| initial | 21 | 21 | 45 | 45 |
| at end of test | 19 | 14.9 | 22 | 8.9 |
| GC analysis (% by weight): |  |  |  |  |
| 1-ring compounds | 1.05 | 3.55 | 3.8 | 11.97 |
| 2-ring compounds | 1.37 | 4.06 | 5.2 | 13.76 |
| heavy products | <0.3 | <0.3 | <0.3 | <0.3 |

In these tables, 1-ring compounds are aromatic compounds such as toluene, xylenes, and ethylbenzene, 2-ring compounds are aromatic compounds such as naphthalene, methylnaphthalene, 1,2,3,4-tetrahydronaphthalene, and methyltetralin, and heavy products are compounds containing more than 3 rings.

What is claimed is:

1. Mono- and polybenzyl-1,2,3,4-tetrahydronaphthalene compositions, characterized in that they comprise a mixture of the following compounds (Y), (Y1), and (Y2):

(Y) is a mixture of monobenzyl-1,2,3,4-tetrahydronaphthalene isomers of formula:

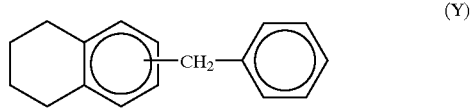

(Y1) is a mixture of monobenzylation compounds of (Y), of formulae:

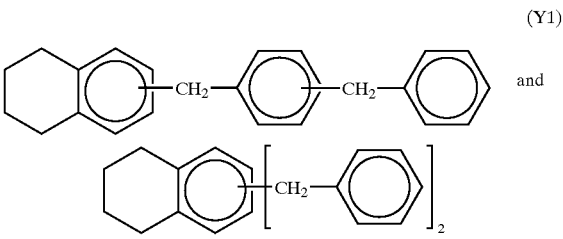

(Y2) is a mixture of mono- or polybenzylation compounds of (Y1), of formulae:

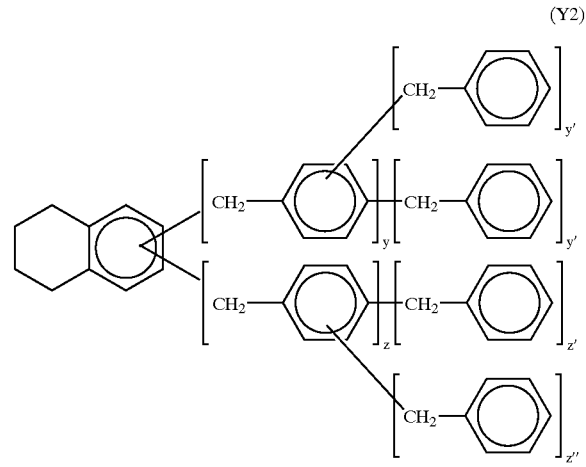

where y and z=0, 1 or 2; y', y", z', z"=0 or 1, with the provisos that y+z is never 0, that y'+y"+z'+z"≧1, and that y+z+y'+y"+z'+z"≧3.

2. Compositions as claimed in claim 1, characterized in that the compounds (Y), (Y1), and (Y2) are present in the following proportions by weight:
   compounds of formula (Y): between 60% and 90%,
   compounds of formula (Y1): between 9% and 35%,
   compounds of formula (Y2): between 0.1% and 10%.

3. Composition as claimed in claim 2, characterized in that it comprises:
   80% by weight of compounds of formula (Y);
   19% by weight of compounds of formula (Y1);
   1% by weight of compounds of formula (Y2).

4. A heat transfer fluid comprising compositions as claimed in claim 1 or a mixture of monobenzyl-1,2,3,4- tetrahydronaphthalene isomers of formula:

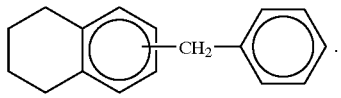
(I)

5. A heat transfer fluid comprising a mixture of monobenzyl-1,2,3,4-tetrahydronaphthalene isomers of formula I:

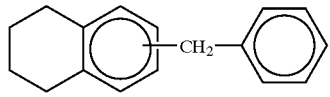
(I)

and wherein said mixture comprises from 30% to 40% by weight of 5-benzyl-1,2,3,4-tetrahydronaphthalene and from 70% to 60% by weight of 6-benzyl-1,2,3,4-tetrahydronaphthalene.

6. A heat transfer fluid as claim in claim 5, wherein the mixture of monobenzyl-1,2,3,4-tetrahydronaphthalene isomers comprises 35% by weight of 5-benzyl-1,2,3,4-tetrahydronaphthalene and 65% by weight of 6-benzyl-1,2,3,4-tetrahydronaphthalene.

7. A process for preparing mono- and polybenzyl-1,2,3,4-tetrahydronaphthalene compositions according to claim 1, comprising acting benzyl chloride with 1,2,3,4-tetrahydronaphthalene in a molar 1,2,3,4-tetrahydronaphthalene/benzene chloride ratio of approximately 4 when preparing compositions comprising a mixture of compounds (Y), (Y1), and (Y2), and at least equal to 4 and, when preparing a monobenzyl-1,2,3,4-tetrahydronaphthalene isomer mixture, in the presence of an inorganic halide or a protic acid at a temperature of between 30° C. and 150° C.

8. The process as claimed in claim 7, characterized in that for preparing a mixture of monobenzyl-1,2,3,4-tetrahydronaphthalene isomers a molar 1,2,3,4-tetrahydronaphthalene/benzyl chloride ratio of equal to 10 is used.

9. The process as claimed in claim 7, characterized in that, when the reaction is at an end, the excess 1,2,3,4-tetrahydronaphthalene is removed, and then the product obtained is subjected to fractional distillation.

10. The process as claimed in claim 7, characterized in that the inorganic halide is ferric chloride.

11. The process according to claim 7, wherein the molar ratio of 1,2,3,4-tetrahydronaphthalene/benzene chloride is between 8 and 12 when preparing a monobenzyl-1,2,3,4-tetrahydronaphthalene isomer mixture.

* * * * *

UNITED STATES PATENT AND TRADEMARK OFFICE
CERTIFICATE OF CORRECTION

PATENT NO. : 6,888,036 B2  Page 1 of 2
DATED : May 3, 2005
INVENTOR(S) : Raymond Commandeur It is certified that error appears in the above-identified patent and that said Letters Patent is hereby corrected as shown below:

Title page,
Item [54], Title, reads "MONO-AND POLYBENZL-1-2-3-4-TETRAHYDRONAPHTALENE COMPOSITIONS, USE OF SAID COMPOSITIONS OR MIXTURE OF MONOBENZYL-1-2-3-4-TETRAHYDRONAPHTALENE AS HEAT TRANSFER FLUID" should read -- MONO-AND POLYBENZL-1-2-3-4-TETRAHYDRONAPHTALENE COMPOSITIONS, USE OF SAID COMPOSITIONS OR MIXTURE OF MONOBENZYL-1-2-3-4-TETRAHYDRONAPHTALENE ISOMERS AS HEAT TRANSFER FLUID --.

Column 8,
Line 32, formula reads:

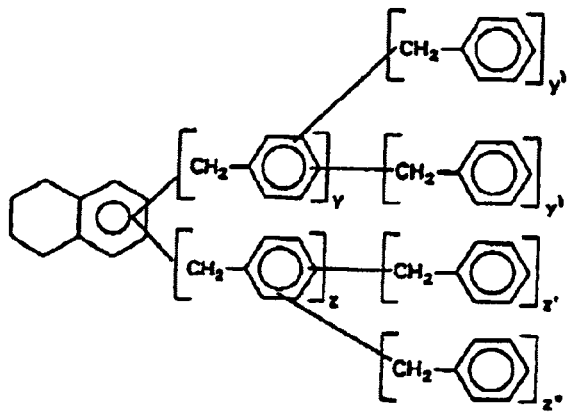

(Y2)

Should read:

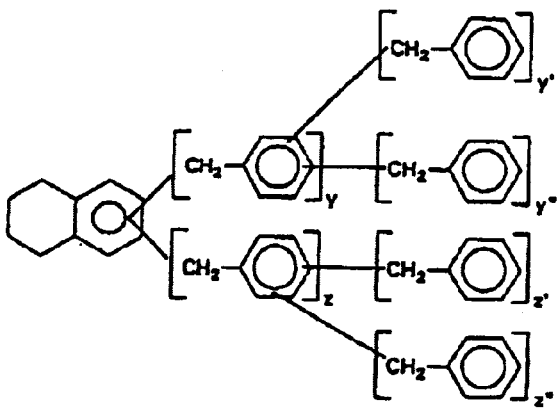

(Y2)

UNITED STATES PATENT AND TRADEMARK OFFICE
CERTIFICATE OF CORRECTION

PATENT NO. : 6,888,036 B2
DATED : May 3, 2005
INVENTOR(S) : Raymond Commandeur

It is certified that error appears in the above-identified patent and that said Letters Patent is hereby corrected as shown below:

Column 10,
Line 1, reads "comprising acting benzyl" should read -- comprising reacting benzyl --.

Signed and Sealed this

First Day of November, 2005

JON W. DUDAS
*Director of the United States Patent and Trademark Office*